(12) United States Patent
Haibel, Jr. et al.

(10) Patent No.: US 6,254,623 B1
(45) Date of Patent: Jul. 3, 2001

(54) ULTRASONIC CLAMP COAGULATOR SURGICAL INSTRUMENT WITH IMPROVED BLADE GEOMETRY

(75) Inventors: Chester G. Haibel, Jr., Mason, OH (US); William A. Bowes, Indianapolis, IN (US); David A. Witt, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/345,277

(22) Filed: Jun. 30, 1999

(51) Int. Cl.⁷ .................................................. A61B 17/32
(52) U.S. Cl. ............................ 606/169; 604/22; 606/171
(58) Field of Search ............................. 606/37, 39, 40, 606/169–172, 151; 604/22; D24/158, 144, 146, 200, 215; D8/417, 101, 98

(56) References Cited

U.S. PATENT DOCUMENTS

| | | | |
|---|---|---|---|
| 2,704,333 | 3/1955 | Calosi et al. ............................ 310/26 |
| 2,990,616 | 4/1961 | Balamuth et al. ........................ 32/26 |
| 3,636,943 | 1/1972 | Balamuth ............................ 128/24 A |
| 3,862,630 | 1/1975 | Balamuth ............................ 128/24 A |
| 5,286,256 | 2/1994 | Mackool ................................ 604/22 |
| 5,322,055 | * 6/1994 | Davison et al. ...................... 606/169 |
| 5,354,265 | 10/1994 | Mackool ................................ 604/22 |
| 5,449,370 | 9/1995 | Vaitekunas ............................ 606/169 |
| 5,505,693 | 4/1996 | Mackool ................................ 604/22 |
| 5,873,873 | 2/1999 | Smith et al. ............................. 606/1 |

\* cited by examiner

Primary Examiner—Henry J. Recla
Assistant Examiner—Lien Ngo
(74) Attorney, Agent, or Firm—Bernard Shay (57) ABSTRACT

An ultrasonic clamp coagulator assembly embodying the principles of the present invention is configured to permit selective cutting, coagulation, and clamping of tissue during surgical procedures. In an ultrasonic blade according to the present invention, the blade is constructed such that the cross-sectional area of the blade is smaller at the proximal end of the compression zone than at the distal end. This performance-enhancing feature creates a more consistent cutting and coagulation of the tissue along the length of the blade reducing the time the blade is in operation and reducing overall heat generation.

7 Claims, 5 Drawing Sheets

ULTRASONIC CLAMP COAGULATOR SURGICAL INSTRUMENT WITH IMPROVED BLADE GEOMETRY

FIELD OF THE INVENTION

The present invention relates, in general, to an improved blade for use in an ultrasonic surgical instrument such as an ultrasonic clamp coagulator and, more particularly, to a blade having improved geometry wherein the cross sectional area of the blade increases from the proximal end of the blade toward the distal end of the blade.

BACKGROUND OF THE INVENTION

Ultrasonic surgical instruments are finding increasingly widespread applications in surgical procedures by virtue of the unique performance characteristics of such instruments. Depending upon the specific instrument configurations and operational parameters, ultrasonic surgical instruments can provide substantially simultaneous cutting of tissue and hemostasis by coagulation, potentially minimizing patient trauma. The cutting action is typically effected by an ultrasonic blade at the distal end of the instrument, with the blade transmitting ultrasonic energy to tissue brought into contact therewith. Ultrasonic instruments of this nature can be configured for open surgical use, or laparoscopic or endoscopic surgical procedures.

In one particular type of ultrasonic instrument, which may be described generally as a clamp coagulator, tissue is forced against an ultrasonic blade by a clamp arm which opposes at least a portion of the ultrasonic blade. In such instruments, the tissue which is positioned between the clamp arm and the blade is compressed against the blade as the clamp arm is closed. Thus the region of the ultrasonic blade opposing the closed clamp arm may be referred to as the compression zone. It is desirable in such an instrument to keep the speed of cutting and coagulation fast to reduce the heat generated in surrounding tissue. The speed at which tissue is cut and coagulated is a function of a number of parameters, including amplitude and frequency of the vibration of the blade and the pressure forcing the tissue against the blade. Instruments such as the clamp coagulator disclosed in U.S. Pat. No. 5,322,055 have blades that have a uniform cross-section in the compression zone. As a result of their uniform compression zone cross-section, the ultrasonic blades illustrated in U.S. Pat. No. 5,322,055 have vibration amplitudes that are greater at their distal ends than at their proximal ends. The result is that cutting and coagulation may take place faster at the distal end of the compression zone than at the proximal end, resulting either in a larger than desired area of coagulation at the distal end of the compression zone or a cut that is shorter and limited to an area near the distal end of the compression zone. Alternatively, tissue positioned at the distal end of the compression zone may be coagulated and cut before tissue at the proximal end is fully coagulated. While none of these limitations is detrimental to the patient, they may result in the surgeon taking smaller bites of the tissue to ensure full coagulation before cutting, thus slowing the surgeon down.

Previous ultrasonic instruments have included ultrasonic blades with variable cross-sectional areas, however, such instruments either do not vary the cross-sectional area of the blade in the compression region of a clamp coagulator. See, for example, U.S. Pat. No. 2,704,333 to Calosi et al. which illustrates an ultrasonic blade which decreases in cross-sectional area from the point of attachment to the distal end. The object of the Calosi invention is to increase vibrational amplitude of the distal end of the ultrasonic blade to effect work upon a piece at the distal end. Calosi teaches placing a higher concentration of mass at the distal end to increase the overall amplitude of the transmitting medium. U.S. Pat. No. 2,990,616, by Balamuth et al. illustrates an ultrasonic cutting tool that has differing geometries to drive vibrations of the tip to effect different characteristics on a cavity being cut into a workpiece. Two U.S. patents by Makool, U.S. Pat. No. 5,354,265 and U.S. Pat. No. 5,505,693, illustrate ultrasonic blades which decrease in cross-sectional area in a region proximal to the useful working area. Davidson et al., U.S., Pat. No. 5,322,055 illustrates ultrasonic blades with varying cross-sectional areas distal to the end of the clamp arm. The particular geometry is added to the tip of the blade so that it is available for useful tasks outside of the compression zone.

It would, therefore, be advantageous to design an ultrasonic clamp coagulator including an ultrasonic blade which has been specifically configured to increase the vibration amplitude in an area adjacent the proximal end of the clamp arm. It would, further, be advantageous to design an ultrasonic clamp coagulator instrument including an ultrasonic blade wherein the vibrational amplitude is greater at the proximal end of the compression zone than the vibrational amplitude in a conventional clamp coagulator. It would further be advantageous to design a clamp coagulator wherein the uniformity of cutting and coagulation within the compression zone is improved over the uniformity obtainable using conventional clamp coagulators.

SUMMARY OF THE INVENTION

An ultrasonic clamp coagulator assembly embodying the principles of the present invention is configured to permit selective cutting, coagulation, and clamping of tissue during surgical procedures. In an ultrasonic blade according to the present invention, the blade is constructed such that the cross-sectional area of the blade is smaller at the proximal end of the compression zone than at the distal end. This performance enhancing feature creates a more consistent cutting and coagulation of the tissue along the length of the blade reducing the time the blade is in operation and reducing overall heat generation.

In particular, in one embodiment of the present invention, an ultrasonic surgical apparatus includes a housing, an ultrasonic drive unit carried by the housing and adapted to generate ultrasonic vibration, an ultrasonic surgical blade having a central axis, a clamp arm, a clamp pad affixed to the clamp arm, a contact region on the outer surface of the ultrasonic surgical blade. In this embodiment, the ultrasonic surgical blade is operatively connected to the ultrasonic transducer, the clamp arm and pad are movable to a closed position opposite the ultrasonic surgical blade substantially parallel to an outer surface of the ultrasonic surgical blade, the blade has a contact region opposite the clamp pad, wherein the blade has a first cross-sectional area within the contact region and adjacent to the proximal end of the contact region and a second cross-sectional area within the contact region and adjacent to the distal end of the contact region, the second cross-sectional area being larger than the first cross sectional area.

Further embodiments of the present invention include ultrasonic surgical clamp coagulator instruments having the following features. A contact region wherein the proximal end of the contact region is aligned with the proximal end of the clamp pad and the distal end of the contact region is aligned with the distal end of the clamp pad. An ultrasonic blade wherein the second cross sectional area is substantially circular in shape. An ultrasonic blade wherein the first cross-sectional area of the ultrasonic blade is substantially circular in shape. A first flat region on a first side of the blade and a second flat region symmetrically positioned on a second side of the blade. A contact surface positioned between the first and second flat regions, the contact surface being narrower at the proximal end of the contact region than at the distal end of the contact region.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

While the present invention is susceptible of embodiments in various forms, there is shown in the drawings and will hereinafter be described a presently preferred embodiment, with the understanding that the present disclosure is to be considered as an exemplification of the invention, and is not intended to limit the invention to the specific embodiment illustrated.

The present invention is particularly directed to an improved ultrasonic surgical clamp coagulator apparatus which is configured for effecting tissue cutting, coagulation, and/or clamping during surgical procedures. The present apparatus can readily be configured for use in both open surgical procedures, as well as laparoscopic or endoscopic procedures. As will become apparent from the following description, the present clamp coagulator apparatus is particularly configured for disposable use by virtue of its straightforward construction. As such, it is contemplated that the apparatus will be used in association with an ultrasonic drive unit of a surgical system, whereby ultrasonic energy from the drive unit provides the desired ultrasonic actuation of the ultrasonic blade of the present clamp coagulator apparatus. It will be appreciated that a clamp coagulator apparatus embodying the principles of the present invention can be configured for non-disposable use, and non-detachably integrated with an associated ultrasonic drive unit. However, detachable connection of the present clamp coagulator apparatus with an associated ultrasonic drive unit is presently preferred for singlepatient use of the apparatus.

Figure 1:
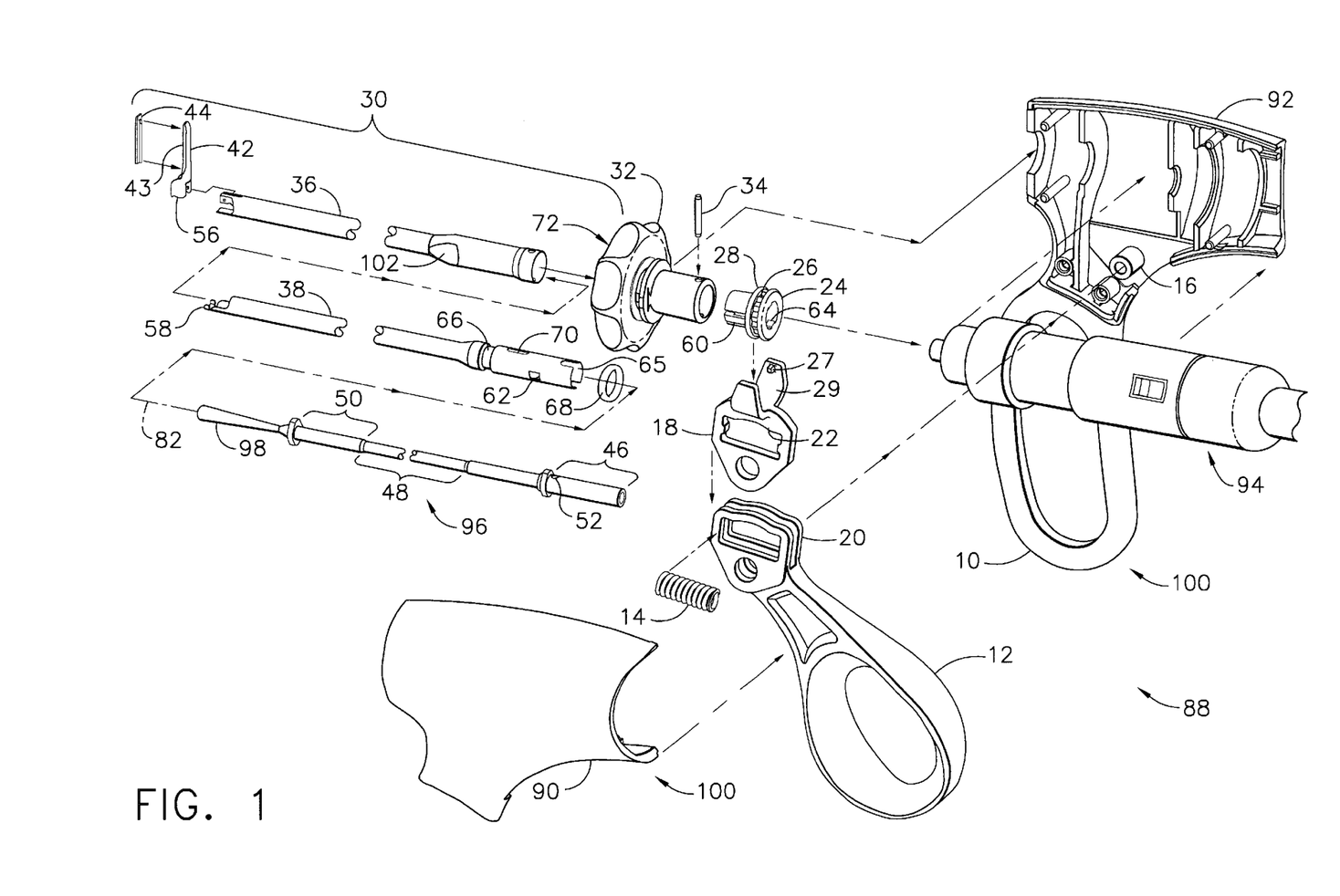
FIG. 1 is an exploded view of the ultrasonic surgical clamp coagulator surgical instrument embodying the principles of the present invention.

With reference first to FIG. 1, therein is illustrated one embodiment of an ultrasonic clamp coagulator apparatus 88 embodying the principles of the present invention. Preferred details of the ultrasonic surgical clamp coagulator apparatus 88, including an elongated portion 30 configured for indexed rotation, embodying the principles of the present invention will be described.

Ultrasonic clamp coagulator apparatus 88 may be attached to an ultrasonic drive unit 94, which can be attached to a waveguide 96 to provide an acoustic assembly of the present surgical system. The acoustic assembly provides ultrasonic energy for surgical procedures when powered by an ultrasonic generator (not shown). It will be noted that in some applications, the ultrasonic drive unit 94 is referred to as a "hand piece assembly" because the surgical instrument is configured such that a surgeon can grasp and manipulate ultrasonic drive unit 94 during various procedures and operations.

Referring now to FIG. 1, an exploded view of ultrasonic clamp coagulator apparatus 88 is illustrated. The proximal end of the ultrasonic clamp coagulator apparatus preferably receives and is fitted to the distal end of the ultrasonic drive unit 94 by insertion of the drive unit into the housing 100 of the apparatus. The ultrasonic clamp coagulator apparatus 88 is preferably attached to and removed from the ultrasonic drive unit 94 as a unit. The ultrasonic clamp coagulator, 88 may be disposed of after a single use.

The ultrasonic clamp coagulator apparatus 88 may include a handle assembly or a housing 100, preferably comprising mating housing portions 90 and 92, and an elongated portion 30. When the present apparatus is configured for endoscopic use, the construction can be dimensioned such that elongated portion 30 has an outside diameter of about 5.5 mm. The elongated portion 30 of the ultrasonic clamp coagulator apparatus 88 extends orthogonally from the housing 100. The elongated portion 30 may include an outer tubular member or sheath 36, an actuating member 38, and the ultrasonic energy transmitting device in the form of a waveguide 96 having a blade 98. The mass of blade 98 is generally dispersed about its longitudinal axis. The sheath 36, the actuating member 38, and the waveguide 96 may be joined together for indexed rotation as a unit (together with ultrasonic drive unit 94) relative to housing 100.

As further illustrated in FIG. 1, the proximal end of the waveguide 96 may be detachably coupled to the ultrasonic drive unit 94 near an anti-node. (For purposes of this disclosure, the term "near" is defined as "exactly at" or "in close proximity to"). The waveguide 96 may have a length substantially equal to an integer number of one-half system wavelengths ($n\lambda/2$). The waveguide 96 is preferably fabricated from a solid core shaft constructed out of material which propagates ultrasonic energy efficiently, such as titanium alloy (i.e. Ti—6Al—4V) or an aluminum alloy. It is contemplated that the waveguide 96 can alternatively be fabricated from any other suitable material.

The waveguide 96 is preferably substantially semi-flexible. It will be recognized that the waveguide 96 can alternatively be substantially rigid or may comprise a flexible wire. The waveguide 96 may be configured to amplify the mechanical vibrations transmitted through the waveguide 96 to the blade 98 as is well known in the art. The waveguide 96 may further have features to control the gain of the longitudinal vibration along the waveguide 96 and features to tune the waveguide 96 to the resonant frequency of the system. Waveguide 96 generally has a first section 46, a second section 48, and a third section 50. The first section 46 of the waveguide extends distally from the proximal end of the waveguide, and has a substantially continuous cross-sectional dimension. The first section 46 may include at least one radial hole or aperture 52 extending diametrically therethrough, substantially perpendicular to the axis of the waveguide 96. The aperture 52 is preferably positioned at a node, but may be otherwise positioned. It will be recognized that the aperture 52 may have any suitable depth and may be any suitable shape. The aperture is configured to receive a connector pin 34, which connects the waveguide 96, the actuating member 38, and the sheath 36 together for conjoint, indexed rotation relative to housing 100. The second section 48 of the waveguide 96 extends distally from the first section 46. The second section 48 may also has a substantially continuous cross-section. The diameter of the second section 48 may also be smaller than the diameter of the first section 46 and smaller than the diameter of the third section 50. As ultrasonic energy passes from the first section 46 of the waveguide 96 into the second section 48, the narrowing of the second section 48 will result in increased amplitude of the ultrasonic energy passing therethrough.

The third section 50 extends distally from the distal end of the second section 48. The third section 50 may also have a substantially continuous cross-section. The third section 50 may also include small diameter changes along its length.

The blade 98 of the waveguide 96, which is attached to the third section 50 may be integral with waveguide 96 and formed as a single unit therewith. The blade 96 may alternately be connected to the waveguide 96 by a threaded connection, or by a welded joint. The distal end of the blade 98 is disposed near an anti-node in order to tune the acoustic assembly to a preferred resonant frequency $f_o$ when the acoustic assembly is not loaded by tissue. When the transducer assembly in ultrasonic drive unit 94 is energized, the distal end of the blade 98 is configured to move longitudinally over a range of, for example, approximately 10–500 microns at a predetermined vibrational frequency $f_o$.

The clamping mechanism of the present clamp coagulator includes a clamp arm 42, which is pivotably moveable, and which may be configured for cooperative action with the blade 98 of the waveguide 96. The clamp arm 42 is pivotally connected at the distal end of the outer tubular sheath 36. The clamp arm 42 may include a clamping portion 43, which extends distally of the pivot axis of the clamp arm for cooperation with blade 98. A clamp pad 44, which may be formed from Teflon or other suitable low-friction material, is mounted on the surface of a clamping portion 43 of the clamp arm 42 for cooperation with the blade 98. Pivotal movement of the clamp arm 42 positions the clamp pad 44 in substantially parallel relation to, and in contact with, the blade 98. The clamp pad 44 is may be provided with a sawtooth-like configuration to enhance the gripping of tissue in cooperation with the blade 98.

Pivotal movement of the clamp arm 42 with the respect to the blade 98 is effected in the illustrated embodiment by the provision of at least one, and preferably a pair of lever portions 56 at the proximal end of clamp arm 42. The lever portions 56 are positioned on respective opposite sides of the waveguide 96 and the blade 98 and are in operative engagement with a drive portion 58 of the actuating member 38. The lever portions 56 can be respectively positioned in a pair of openings defined by the drive portion 58 or otherwise suitably mechanically coupled therewith, whereby reciprocal movement of the actuating member acts through the drive portion 58 and the lever portions 56 to pivot the clamp arm 42. In the illustrated embodiment, the actuating member 38 acts on the lever portions 56 moving clamp arm 42 in a direction toward blade 98. Maximization of the moment arm thus created facilitates creation of the desired compression clamping force against blade 98 within the confines of an instrument having a relatively small cross-section.

The reciprocal movement of the actuating member 38 is effected by the provision of a drive collar 24 mounted on the proximal end of the actuating member 38 for conjoint rotation. To this end, the drive collar 24 includes a pair of diametrically opposed axially extending arms 60 each having a drive lug, with the drive lugs being biased by the arms 60 into engagement with suitable openings 62 in the proximal portion of actuating member 38. Rotation of the drive collar 24 together with the actuating member 38 is further effected by the provision of a pair of keys 64 diametrically engageable with suitable openings 65 defined by the proximal end of the actuating member 38. A circumferential groove 66 on the actuating member 38 receives an O-ring 68 for engagement with the inside surface of the outer sheath 36. Rotation of the actuating member 38 together with tubular outer sheath and inner waveguide is facilitated by connector pin 34. As illustrated in FIG. 1, the actuating member 38 includes an elongated slot 70 through which the connector pin 34 extends to accommodate reciprocal movement of the actuating member relative to the outer tubular sheath and inner waveguide.

A rotation knob 32 mounted on the sheath 36 facilitates rotation positioning of the elongated portion 30 with respect to the housing 100 of the clamp coagulator apparatus. Connector pin 34 preferably joins knob 32 to sheath 36, actuating member 38, and waveguide 96 for rotation as a unit relative to housing 100 while hub portion 72 of the rotation knob 32 acts to rotatably mount the tubular 36, the actuating member 38, and the waveguide 96 (as a unit with knob 32), on the housing 100. The drive collar 24 facilitates the pivotal movement of the clamp arm 42 by reciprocation of actuating member 38. Drive yoke 18 is operatively connected with an operating lever 12, with the operating lever 12 thus interconnected with the actuating member 38 via drive yoke 18 and drive collar 24. The operating lever 12 is pivotally connected to the housing 100 of the apparatus (by a pivot mount 16) for cooperation in a scissors-like fashion with a handgrip portion 10 of the housing 100. Movement of the operating lever 12 towards handgrip portion 10 translates actuating member 38 proximally, thereby pivoting clamp arm 42 toward blade 98. Operative connection of the drive yoke 18 with the operating lever 12 is provided by a spring 14 which may be a compression coil spring. The spring 14 fits within a spring slot 22 in drive yoke 18, which, in turn, is positioned between a pair of spring retainer flanges 20 of the operating lever 12. The drive yoke 18 is pivotally movable with respect to the spring flanges 20 (about pivot mount 16 of housing 100) in opposition to the spring 14, which bears against the surfaces of the spring slots in each of the spring flanges 20. In this manner, the force which can be applied to the actuating member 38, by pivotal movement of operating lever 12 acting through drive yoke 18 and drive collar 24, is limited by the force with which spring 14 exerts against the spring flanges 20.

Indexed rotation position of the elongated portion 30 of the ultrasonic clamp coagulator apparatus 88 is provided by detents 27. Specifically, the drive collar 24 includes a pair of axially spaced apart drive flanges 28. A detent-receiving surface is provided between the drive flanges 28, and includes a plurality of circumferentially spaced teeth 26 which may be detent-receiving depressions generally about the periphery of the drive collar 24.

Index rotational movement is further achieved by the provision of at least one, and preferably a pair, of diametrically opposed detents 27 respectively provided on cantilevered yoke arms 29 of drive yoke 18. By this arrangement, the yoke arms 29 are positioned between the drive flanges 28 for engagement with the confronting surfaces thereof. Yoke arms 28 bias the detents 27 into engagement with the drive collar 24. Indexed relative rotation is thus achieved, with the detents 27 of the yoke arms 29 cooperating with the drive flanges 28 for effecting reciprocation of the actuating member 38. The drive yoke 18 may be formed from suitable polymeric material, with the biasing force created by the yoke arms acting on the detents thereof cooperating with the radial depressions defined by the drive collar to resist relative rotational torque less than about 1 to 2 inch-pounds. As such, the elongated portion 30 of the clamp coagulator apparatus is maintained in any of its selected indexed rotational positions, relative to housing 100, unless a torque is applied (such as by rotation knob 32) exceeding this predetermined torque level. A snap-like indexing action is thus provided.

Rotation of the elongated portion 30 of the ultrasonic clamp coagulator apparatus 88 is preferably effected together with a relative rotational movement of ultrasonic drive unit 94 with respect to apparatus housing 100. In order to join the elongated portion 30 to the ultrasonic drive unit 94 in ultrasonic-transmitting relationship, the proximal portion of the sheath 36 is preferably provided with a pair of wrench flats 102. The wrench flats 102 allow torque to be applied by a suitable torque wrench (not shown) or the like to join waveguide 96 to ultrasonic drive unit 94. The ultrasonic drive unit 94, as well as the elongated portion 30, are thus rotatable relative to housing 100 as a unit by suitable manipulation of rotation knob 32. The interior of housing 100 is dimensioned to accommodate such relative rotation of the ultrasonic drive unit 94.

Figures 2, 3:
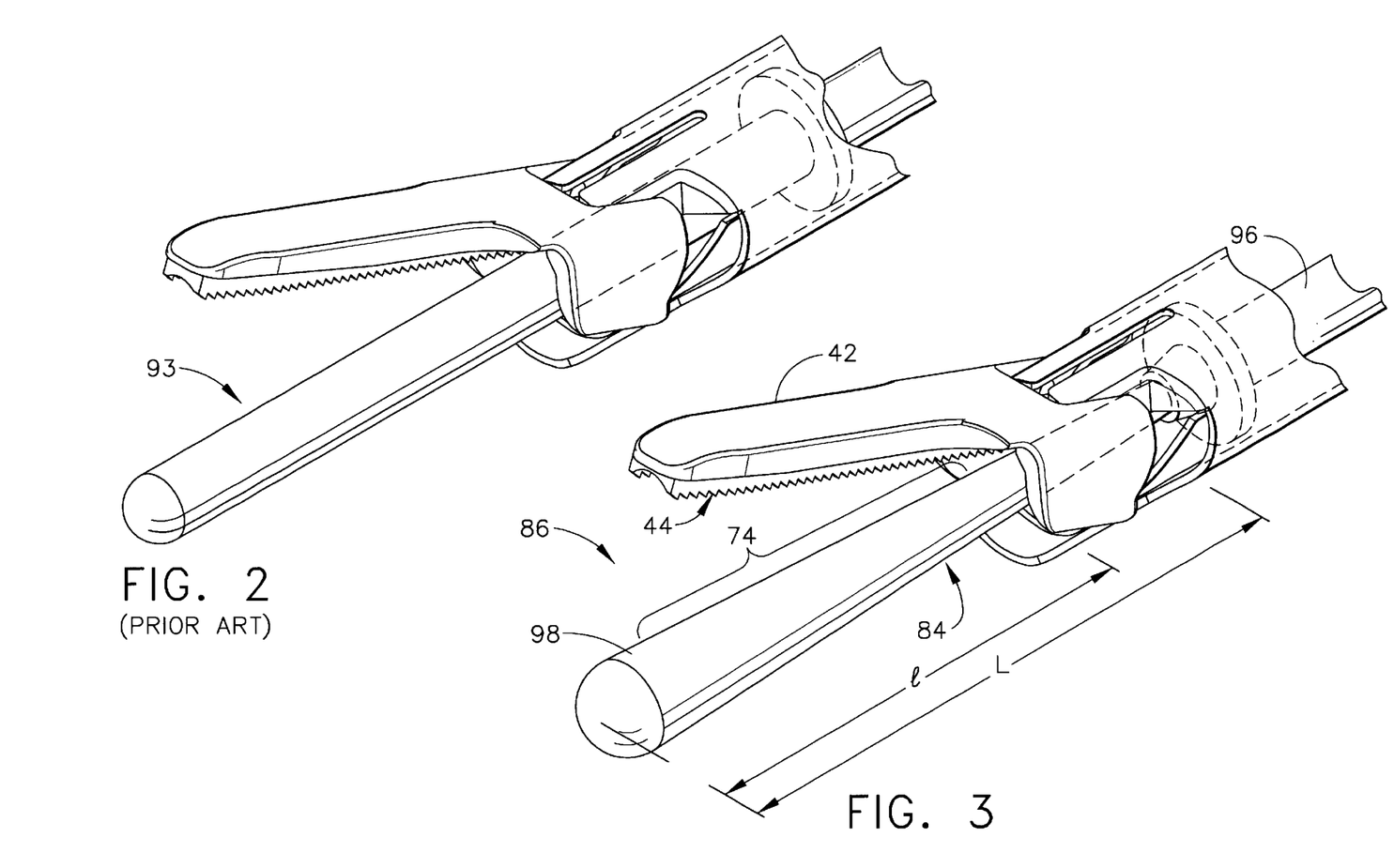
FIG. 2 is a perspective view depicting the blade, the clamp arm, and the inner tube of a prior art instrument.
FIG. 3 is a perspective view depicting the blade, the clamp arm, and the inner tube of an embodiment of the current invention.
Figure 4:
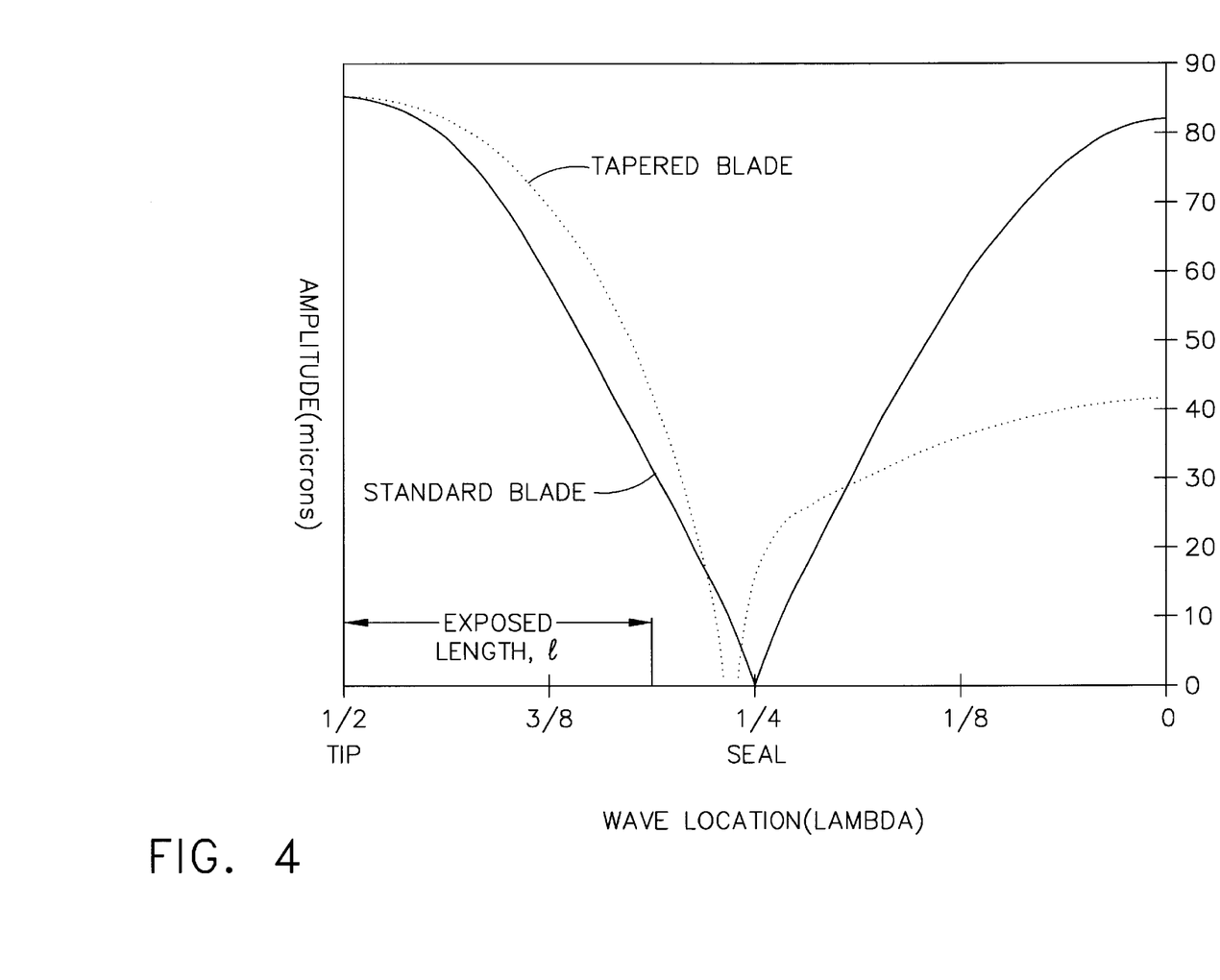
FIG. 4 is a plot of the calculated vibration amplitudes of particular points of the blade in microns for the prior art blade and an embodiment of the current invention versus the distance along the axis of the blade expressed as a fraction of the wavelength of the applied vibration.

FIG. 3 illustrates a blade wherein a cross-sectional profile taken near the distal end 86 of contact zone 74 defines a circle with a larger circumference than the circumference of a cross-sectional profile taken at a point closer to the proximal end 84 of contact zone 74. In the embodiment of the invention illustrated in FIG. 3, the circumferences of defined circles within contact zone 74 increase as one moves distally along the axis of the blade 98, allowing such a blade to be easily created using a lathe. FIG. 3 displays an embodiment of the present invention wherein contact zone 74 is the portion of blade 98 which is in contact with or directly opposite clamp pad 44 when clamp arm 42 is closed. Contact zone 74 may also be referred to as a compression zone. In the embodiment of the invention illustrated in FIG. 3, a cross-section taken near a distal end 86 of contact zone 74 has a larger area than does a cross-section taken closer the proximal end 84 of contact zone 74. In operation, the clamp arm 42 with its associated clamp pad 44 compresses the tissue to be cut and coagulated against the blade 98. When the clamp arm 42 with its associated clamp pad 44 is closed down, clamp arm 42 is parallel to the outside surface of the blade 98. Ultrasonic vibrations from ultrasonic transducers in ultrasonic drive unit 94 excite the blade 98 in a manner that causes an excursion of each point along the length of the blade parallel to axis 82. The excursion has an amplitude that varies with the distance along the length of the blade. The solid line in FIG. 4 shows the calculated axial vibration amplitude as a function of the distance along the length of a standard blade 93, such as the standard blade illustrated in FIG. 2 having a uniform cross section along the length of the contact zone 74. Referencing the solid line of FIG. 4, it is noticed that the vibration of the exposed length of the blade as a large amplitude at the distal tip near a vibration antinode and decreases at points proximal to the distal tip which are closer to a node. If, as in a blade 98 designed according to the present invention, the cross-sectional area and its associated mass per unit length increases from the proximal end 84 of the contact zone 74 to the distal end 86 of the contact zone 74, the more proximal end 84 of the blade will have an increased vibratory amplitude relative to that of the distal end 98. The increased relative vibratory amplitude at the proximal end 84 of a contact zone 74 in a blade designed according to the present invention is shown by the dotted line of FIG. 4. Therefore, in an ultrasonic clamp coagulator including a blade 98 according to the present invention, the energy applied to tissue in the contact zone 74 by the vibratory motion is more uniform along the entire length of the blade 98. Because the effect on tissue is more uniform along the length of contact zone 74, the surgeon will not have to wait as long for the lower amplitude proximal side of the blade 98 to cut and coagulate the tissue. An improved blade configuration according to the present invention would, therefore, because of less time spent using the instrument on the tissue, causes less overall heat generation.

A further benefit of the improved geometry in a blade 98 designed according to the present invention is that the smaller cross-sectional area nearer the proximal end 84 of the contact zone 74 has a smaller radius in the direction towards the clamp arm than the cross-sectional area nearer the distal end 86. The smaller radius increases the pressure on the tissue compressed between the blade 98 and the clamp pad 44 in the contact region 74 nearer the proximal end 84. The sharper, smaller radius causes faster cutting while still coagulating, giving the desired effect of a faster cut at the proximal end and hence more uniform performance along the length of the blade.

Figures 5, 6, 7:
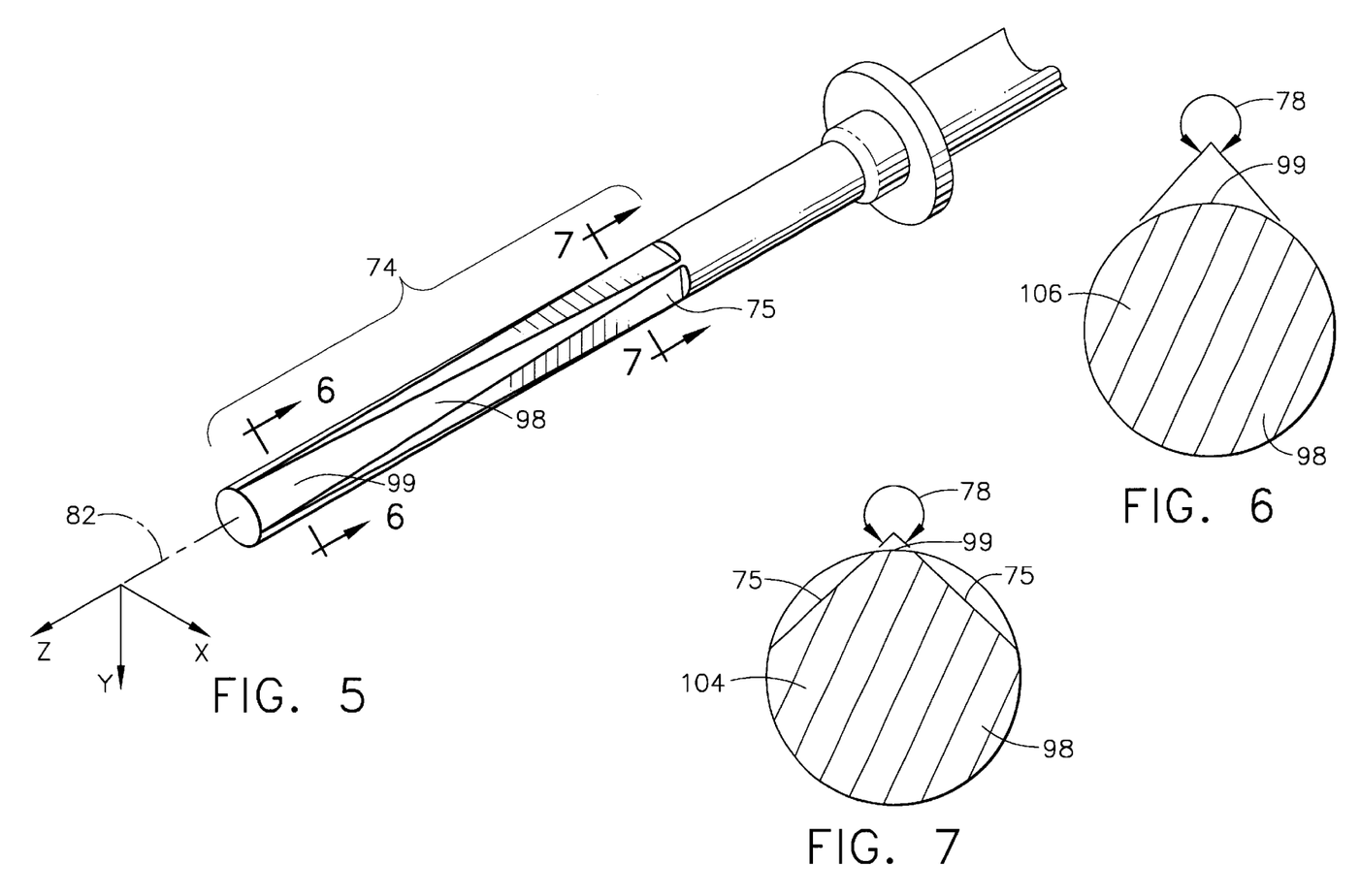
FIG. 5 is a perspective view of a further embodiment of an ultrasonic blade according to the present invention depicting a variable width contact portion along the length of the compression zone.
FIG. 6 is a cut away view of the blade illustrated in FIG. 5 along 6—6 in FIG. 5.
FIG. 7 is a cut away view of the blade illustrated in FIG. 5 along 7—7 in FIG. 5.

FIG. 5 illustrates an alternative embodiment of blade 98 according to the present invention. Blades 98 designed according to the present invention may use various geometrical constructions to attain the goal of having a smaller cross-sectional area near the proximal end of the contact zone 74 than near the distal end of the contact zone. FIG. 5 displays a uniformly circular blade 98 modified by removing a slight amount of material with a flat cutter such as an end mill at the distal end of the blade 98 and removing an increasing amount of material by plunging the cutter towards the longitudinal axis 82 as it moves towards the proximal end of the blade 98. As illustrated in FIGS. 6 and 7, performing such an action at two different circumferential locations results in a smaller cross-sectional area 104 in the proximal portion than the cross-sectional area 106 in a distal portion of blade 98. This action also creates two flats 75 that remain at the same subtended angle 78 with respect to each other at any point along the longitudinal axis 82 of the blade.

The embodiment of the invention illustrated in FIG. 5 is made by first making a cut into a cylindrical blade with the cutter shifted in the positive X direction relative to the longitudinal axis 82 and tilted clockwise. The cutter is plunged deeper as it progresses across the surface of the blade, making the flat on the positive side of the blade shown in FIG. 5. A cut is then taken in the plane perpendicular to the. first cut. This second cut is necessary to achieve the appearance shown in FIG. 5, but the embodiment does not require it. The process is repeated by moving the cutter the same distance in the negative X direction with the cutter tilted counterclockwise, making the second flat. In the embodiment illustrated, a varying width contact zone 74 is formed having a contact surface 99 that is wide at the distal end because of the near circular profile, with only very small linear sections. In the embodiment of the invention illustrated in FIG. 5, the contact width of contact zone 74 is narrow near the proximal end of blade 98 with the sharply sloping sides not allowing tissue contact across as wide an area, thus increasing the contact pressure at the proximal end of the contact zone 74 over the contact pressure exerted at the distal end of the contact zone 74. The compressive nature of tissue will allow it to follow the contour of the contact surface 99.

Figures 8, 9, 10:
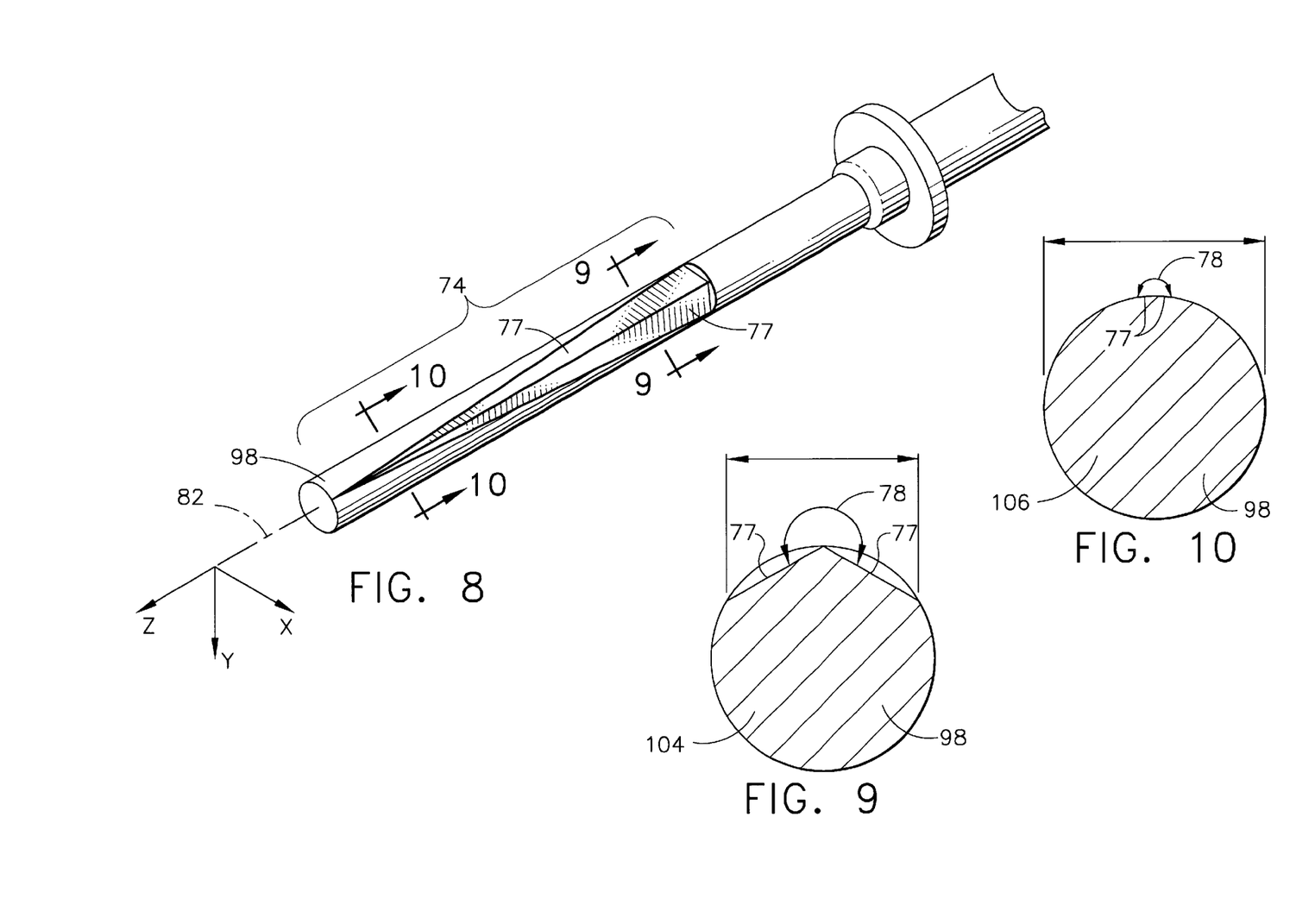
FIG. 8 is a perspective view of a further embodiment of an ultrasonic blade according to the present invention depicting a variable width contact portion along the length of the compression zone.
FIG. 9 is a cut away view of the blade illustrated in FIG. 8 along 9—9 in FIG. 8.
FIG. 10 is a cut away view of the blade illustrated in FIG. 8 along 10—10 in FIG. 8.

FIG. 8 illustrates an alternative embodiment of blade 98 according to the present invention. As described with respect to FIG. 5, blades 98 designed according to the present invention may use various geometrical constructions to attain the goal of having a smaller cross-sectional area near the proximal end of the contact zone 74 than near the distal end of the contact zone. FIG. 8 displays a uniformly circular blade 98 modified, in a manner similar to the method used to create the blade 98 illustrated in FIG. 5, by removing a slight amount of material with a flat cutter such as an end mill at the distal end of the blade 98 and removing an increasing amount of material by plunging the cutter towards the longitudinal axis 82 as it moves towards the proximal end of the blade 98. As illustrated in FIGS. 9 and 10, performing such an action at two different circumferential locations results in a smaller cross-sectional area 104 in the proximal portion than the cross-sectional area 106 in a distal portion of blade 98. This action also creates two flats 77 that remain at the same subtended angle 78 with respect to each other at any point along the longitudinal axis 82 of the blade. The embodiment of the invention illustrated in FIG. 8 is made by first making a cut into a cylindrical blade with the cutter shifted in the positive X direction relative to the axis 82 and tilted clockwise. The cutter is plunged deeper as it progresses across the surface of the blade, making the flat on the positive side of the blade shown in FIG. 8. A cut is then taken in the plane perpendicular to the first cut. This second cut is necessary to achieve the appearance shown in FIG. 8, but the embodiment does not require it. The process is repeated by moving the cutter the same distance in the negative X direction with the cutter tilted counterclockwise, making the second flat. In the embodiment illustrated, a fixed width contact zone is formed with a contact surface 97 that is narrow along its entire length.

Thus the present surgical clamp coagulator apparatus is configured for highly efficient and versatile use, with the construction sufficiently straightforward and economical in configuration to permit single patient use. The varying cross-sectional area with its associated contact width and mass per unit length is easily created using standard machining, casting, or metal injection molding techniques. By virtue of the advantages offered by the new configuration, a more even tissue cut and coagulation can be achieved along the length of the improved blade.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. Ultrasonic surgical apparatus comprising:

a housing;

an ultrasonic drive unit carried by said housing and adapted to generate ultrasonic vibration;

an ultrasonic surgical blade having a central axis, wherein said ultrasonic surgical blade is operatively connected to said ultrasonic transducer, said ultrasonic blade being adapted to receive ultrasonic vibration from said ultrasonic transducer and to vibrate in a longitudinal directional substantially parallel to said central axis;

a clamp arm carried by said apparatus and movable to a closed position opposite said ultrasonic surgical blade substantially parallel to an outer surface of said ultrasonic surgical blade;

a clamp pad affixed to said clamp arm, said clamp pad having a proximal end and a distal end;

a contact region on said outer surface of said ultrasonic surgical blade comprising a portion of said outer surface which is opposite said clamp pad, wherein said contact region has a proximal end and a distal end wherein said blade has a first cross-sectional area within said contact region and adjacent to said proximal end of said contact region and a second cross-sectional area within said contact region and adjacent to said distal end of said contact region, said second cross-sectional area being larger than said first cross-sectional area.

2. An ultrasonic surgical instrument according to claim 1 wherein said proximal end of said contact region is aligned with said proximal end of said clamp pad and said distal end of said contact region is aligned with said distal end of said clamp pad.

3. An ultrasonic surgical instrument according to claim 1 wherein said second cross sectional area is substantially circular in shape.

4. An ultrasonic surgical instrument according to claim 1 wherein said first cross-sectional area is substantially circular in shape.

5. An ultrasonic surgical instrument according to claim 1 wherein said blade further comprises:

a first flat region on a first side of said blade; and a second flat region on a second side of said blade, wherein said first and said second flat regions are symmetrical about a second axis of said blade wherein said second axis is perpendicular to said central axis and parallel to said first and second cross sectional areas.

6. An ultrasonic instrument according to claim 5 wherein said first flat region and said second flat region intersect at said outer surface of said ultrasonic surgical blade.

7. An ultrasonic surgical instrument according to claim 1 wherein said ultrasonic surgical blade has a contact surface positioned between said first and second flat regions, said contact surface being narrower at said proximal end of said contact region than at said distal end of said contact region.

* * * * *